(12) United States Patent
Staats et al.

(10) Patent No.: US 6,764,466 B1
(45) Date of Patent: Jul. 20, 2004

(54) ADAPTER AND SYRINGE FOR FRONT-LOADING MEDICAL FLUID INJECTOR

(75) Inventors: Peter F. Staats, Loveland, OH (US); Dane J. Battiato, Cincinnati, OH (US)

(73) Assignee: Liebel Flarsheim Company, Cincinnati, OH (US)

( * ) Notice: Subject to any disclaimer, the term of this patent is extended or adjusted under 35 U.S.C. 154(b) by 0 days.

(21) Appl. No.: 10/386,995

(22) Filed: Mar. 12, 2003

Related U.S. Application Data

(62) Division of application No. 09/648,268, filed on Aug. 25, 2000, now Pat. No. 6,533,758, which is a continuation of application No. 08/896,698, filed on Jul. 18, 1997, now abandoned.

(51) Int. Cl.[7] .............................................. A61M 37/00
(52) U.S. Cl. ........................ 604/154; 604/218; 604/228; 604/533
(58) Field of Search ................................ 604/151, 152, 604/154, 110, 155, 131, 905, 181, 187, 218, 227, 228, 229, 533, 534, 535, 536, 232

(56) References Cited

U.S. PATENT DOCUMENTS

| | | | |
|---|---|---|---|
| 4,636,198 A | * 1/1987 | Stade | 604/154 |
| 4,869,720 A | 9/1989 | Chernack | 604/228 |
| 5,300,031 A | 4/1994 | Neer et al. | 604/154 |
| 5,383,858 A | 1/1995 | Reilly et al. | 604/152 |
| 5,451,211 A | * 9/1995 | Neer et al. | 604/154 |
| 5,520,653 A | 5/1996 | Reilly et al. | 604/152 |
| 5,535,746 A | 7/1996 | Hoover et al. | 604/187 |
| 5,947,929 A | 9/1999 | Trull | 604/152 |
| 6,080,136 A | 6/2000 | Trull et al. | 604/218 |

* cited by examiner

Primary Examiner—Brian L. Casler
Assistant Examiner—Jeremy Thissell
(74) Attorney, Agent, or Firm—Wood, Herron & Evans, LLP

(57) ABSTRACT

Adapters for use with an angiographic injector. A face plate adapter includes a channel for receiving a rearward end of a syringe. First and second mounting flanges on the adapter overlay a portion of the channel, to cooperate with mounting flanges on a rearward end of the syringe, so that the syringe mounting flanges may be inserted between the adapter mounting flanges, and then rotated in the channel behind the adapter mounting flanges, to thereby lock the syringe to the adapter. The adapter further includes one or more locking pins, which in a locked position extend across the channel, to block the syringe from rotating in the channel and thereby prevent a syringe from being dismounted from the adapter. A collar incorporated in the adapter interacts with a drive ram of the injector to move the locking pins into their locked position whenever the ram is forward of a rearwardmost position. A ram tip adapter includes a movable member having a connector for engaging a connector on a rearward face of a plunger, and a cam surface for interacting with the face plate adapter. The interaction between the cam surface and the face plate adapter causes the connector of the movable member to move to an engaging position in which the connector engages with the connecting structure of the syringe, only when the ram is forward of its rearwardmost position.

8 Claims, 3 Drawing Sheets

ADAPTER AND SYRINGE FOR FRONT-LOADING MEDICAL FLUID INJECTOR

CROSS REFERENCE TO RELATED APPLICATIONS

This application is a divisional of a continued prosecution application of U.S. patent application Ser. No. 09/648,268, filed Aug. 25, 2000, now U.S. Pat. No. 6,533,758, issued Mar. 18, 2003, which is a continuation of U.S. patent application Ser. No. 08/896,698, filed Jul. 18, 1997, now abandoned, entitled ADAPTER AND SYRINGE FOR FRONTLOADING MEDICAL FLUID INJECTOR, which is incorporated herein by reference in its entirety. These applications are related to U.S. patent application Ser. No. 09/665,374, filed Aug. 5, 2002, as a continued prosecution application of a U.S. patent application originally filed May 12, 2000, which is a continuation of U.S. patent application Ser. No. 08/896,695, filed Jul. 18, 1997, now abandoned, entitled ADAPTER AND SYRINGE FOR FRONT-LOADING MEDICAL FLUID INJECTOR, by Frank Fago, Robert Ziemba and Gary Wagner, which is incorporated herein by reference in its entirety.

FIELD OF THE INVENTION

The present invention relates to medical fluid injectors for injecting medical fluid into patients.

BACKGROUND OF THE INVENTION

Injectors are devices that expel fluid, such as contrast media, from a syringe and through a tube into an animal. The injectors are provided with an injector unit, usually adjustably fixed to a stand or support, and have a drive ram that couples to the plunger of the syringe to drive it forward to expel fluid into the tube, or to drive the plunger rearward to draw fluid into the syringe to fill it. Usually the syringe is a disposable replacement type.

U.S. Pat. No. 5,300,031, which is assigned to the same assignee as this application, discloses a front-loading injector. This injector has a pressure jacket mounted to its front face for receiving a syringe. A syringe having an open back end is inserted into the pressure jacket and coupled to the pressure jacket by a rotating motion. This same rotating motion causes the plunger in the syringe to couple to the end of the ram. The pressure jacket supports the side walls of the syringe against injection pressure during operation of the injector. After an injection, a reverse rotating motion unlocks the syringe from the pressure jacket and releases the plunger from the ram, so the syringe can be removed and replaced.

An advantage of this front-loading structure, as compared to prior, breach-loading structures, is that the syringe may be disconnected and removed from the injector after an injection, while the ram is in its forwardmost position. Furthermore, while the ram remains in its forwardmost position, a new syringe may be inserted into the pressure jacket, over the ram, and locked to the pressure jacket and ram. Then, filling of the syringe for the new injection can immediately commence. When loading and unloading operations are performed with the ram in a forward position, the pressure jacket serves as a guide to prevent the ram from contacting the internal surfaces of the syringe, thus preserving sterility of the internal surfaces of the syringe. Accordingly, removal and replacement of a syringe can be accomplished without extraneous movement of the ram and without risks of loss of sterility.

A second front-loading injector structure is disclosed in U.S. Pat. No. 5,383,858. This front loading injector structure is similar in many respects to that disclosed in U.S. Pat. No. 5,300,031, with the main difference that the injector of U.S. Pat. No. 5,383,858 does not include a pressure jacket on the front surface thereof. Rather, the syringe is made of a hard plastic material which is deemed sufficiently self-supporting to withstand injection pressures. In the front-loading injector of U.S. Pat. No. 5,383,858, the syringe and injector, and the plunger and ram, are connected to each other by a single twisting motion, and disconnected from each other by a reverse twisting motion; thus, the connection and disconnection procedures are similar to that used by the injector of U.S. Pat. No. 5,300,031.

SUMMARY OF THE INVENTION

A disadvantage of the injector of U.S. Pat. No. 5,383,858, is that, while it is possible to remove the syringe of U.S. Pat. No. 5,383,858 from the injector, while the ram is in a forward position, and to insert a new syringe to the injector while the ram remains in this forward position, and even tempting to do so, this procedure for loading and unloading a syringe is not advisable. The injector of U.S. Pat. No. 5,383,858 lacks a pressure jacket or any other mechanism for preventing the internal surfaces of the syringe from contacting the end of the drive ram. Accordingly, it is likely that a user of the injector, attempting to remove and replace a syringe on this injector with the ram in its forward position, will accidentally contact the interior surface of the syringe with the end of the ram, contaminating the interior of the syringe and risking infection to the patient. Unfortunately, however, users of the injector of U.S. Pat. No. 5,383,858, particularly those users familiar with the injector shown in U.S. Pat. No. 5,300,031, are likely to be tempted to remove and replace syringes with the ram forward.

Thus, there is a need for an adapter for the injector of U.S. Pat. No. 5,383,858, which can be fitted to that injector to prevent the user of the injector from attempting to remove the syringe with the ram forward of its rearwardmost position.

In accordance with a first aspect of the present invention, an adapter is incorporated into the face plate of the injector of U.S. Pat. No. 5,383,858, to prevent the user of the injector from rotating the syringe when the ram of the injector is at other than its rearwardmost position. Specifically, the adapter includes a channel for receiving a rearward end of a syringe. This channel interacts with mounting structure on a rearward end of the syringe, so that the syringe may be inserted into and then rotated in the channel to lock the syringe to the adapter. The adapter further includes one or more locking pins, which in a locked position extend across the channel, to block the syringe from rotating in the channel and thereby prevent a syringe from being mounted to or dismounted from the adapter, and which in an unlocked position do not extend across the channel and do not block the syringe from rotating in the channel to mount or dismount to or from the adapter. A cam member incorporated in the adapter interacts with a drive ram of the injector to move the locking pins between the locked and unlocked positions, so that the locking pins move into their locked position whenever the ram is forward of a rearwardmost position.

In specific embodiments, the cam member is a collar, which fits over the tip of the ram. The locking pins are integral with the collar, and extend from the collar through the adapter and, in their locked position extend into the channel on the front surface of the adapter. Resilient elements (e.g., springs) mounted in the adapter generate a force tending to push the collar forward to the locked position. The collar interacts with the ram such that when the ram is withdrawn from the syringe, the ram engages the collar and withdraws the collar and the locking pins integral therewith rearwardly into the injector. This rearward motion draws the locking pins out of the channel on the front surface of the injector, permitting a syringe to be mounted to the injector. A ram tip extender is attached to the ram disclosed in U.S. Pat. No. 5,383,858, which extender includes cam surfaces for engaging the collar to draw the collar backward.

In accordance with another aspect of the present invention, a novel ram tip is used in connection with a front loading injector. This ram tip includes movable member having a connector for engaging a connecting structure on a rearward face of a plunger, and a cam surface for interacting with the injector to move the movable member when the ram tip is in a rearward position. The interaction between the cam surface and the injector causes the connector of the movable member to move between an engaging position in which the connector engages with the connecting structure of the syringe, and a disengaging position in which the connector does not engage the connecting structure of the syringe.

In specific embodiments, the ram tip comprises a second movable member, including a second connector and a second cam surface, where the interaction of the second cam surface with the injector causes the second connector of the second movable member to move between an engaging position in which the second connector engages with the connecting structure of the syringe, and a disengaging position in which the second connector does not engage the connecting structure of the syringe.

The movable members move by rotating between the engaging and disengaging positions. The connectors on the movable members are hooks, which project radially outward when the movable members are rotated into their engaging positions, and are positioned at a radially inward position when the movable members are rotated to their disengaging positions. The cam surfaces are ramp members which contact mating ramp members on a front surface of the injector, causing the movable members to rotate inwardly toward their disengaging positions. A resilient element produces a force tending to position the movable members in their engaging positions absent a counteracting force applied to the cam surfaces.

The above and other objects and advantages of the present invention shall be made apparent from the accompanying drawings and the description thereof.

BRIEF DESCRIPTION OF THE DRAWING

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF SPECIFIC EMBODIMENTS

Figure 1:
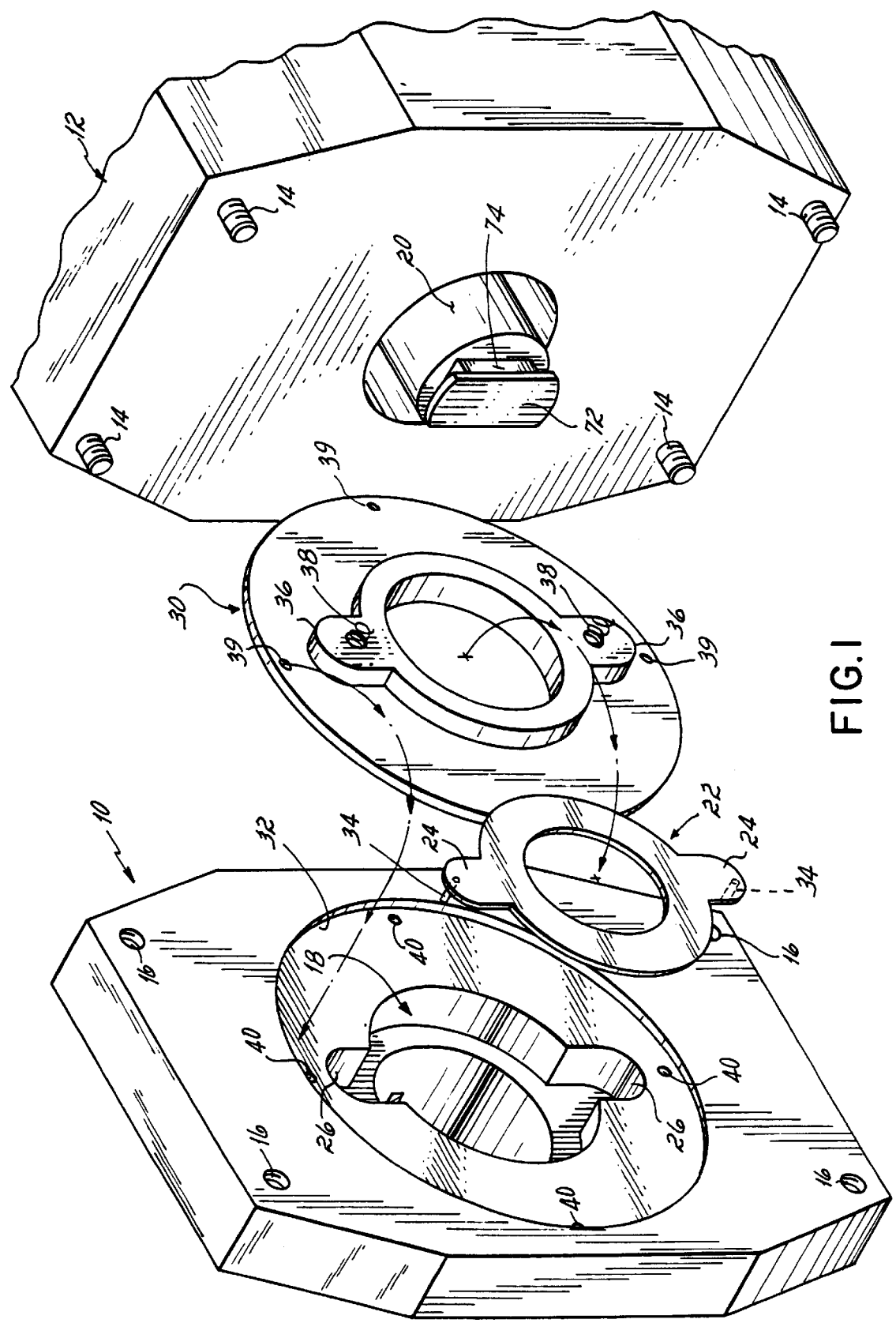
FIG. 1 is a disassembled perspective view of a front surface of the injector described in U.S. Pat. No. 5,383,858, and a replacement face plate for mounting thereto.

Referring to FIG. 1, in accordance with principles of the present invention, a front loading injector such as that disclosed in U.S. Pat. No. 5,383,858 is retrofitted with a replacement face plate 10. Injector 12 includes screws 14 running the length thereof for mounting a face plate to injector 12. Face plate 10 includes apertures 16 in registry with screws 14 to permit face plate 10 to be mounted to injector 12.

Face plate 10 includes a central aperture 18 positioned in registration with a ram 20 of the injector 12. Face plate 10 is assembled by inserting a collar 22 into central aperture 18 with ears 24 of collar 22 in registry with recesses 26 in face plate 10. Cap 30 fits over a recessed area 32 of face plate 10 to retain collar 22 within face plate 10. Collar 22 includes, on a forward surface thereof locking pins 34. Locking pins 34 extend outwardly from a front surface of face plate 10 to perform a locking function as described in further detail below. Cap 30 includes on a forward surface thereof, a mounting feature 36 which is shaped conformally with aperture 18 and recesses 26. Mounting feature 36 further supports springs 38 which engage a rearward surface of collar 22 to generate a force tending to push collar 22 forwardly into face plate 10. (In alternative embodiments, other resilient elements, such as a foam rubber block, might be used in place of springs 38 to generate forward forces against collar 22.)

Face plate 10 is assembled by inserting collar 22 into aperture 18, and then placing cap 30 into recessed area 32 to hold collar 22 in place. Mounting screws 37 (FIGS. 3 and 4) are then inserted through holes 39 in cap 30 into threaded apertures 40 in face plate 10. The face plate after assembly is itself assembled to injector 12 by placing apertures 16 in registry with screws 14 and tightening screws 14 to hold face place 10 onto injector 12.

Figure 2:
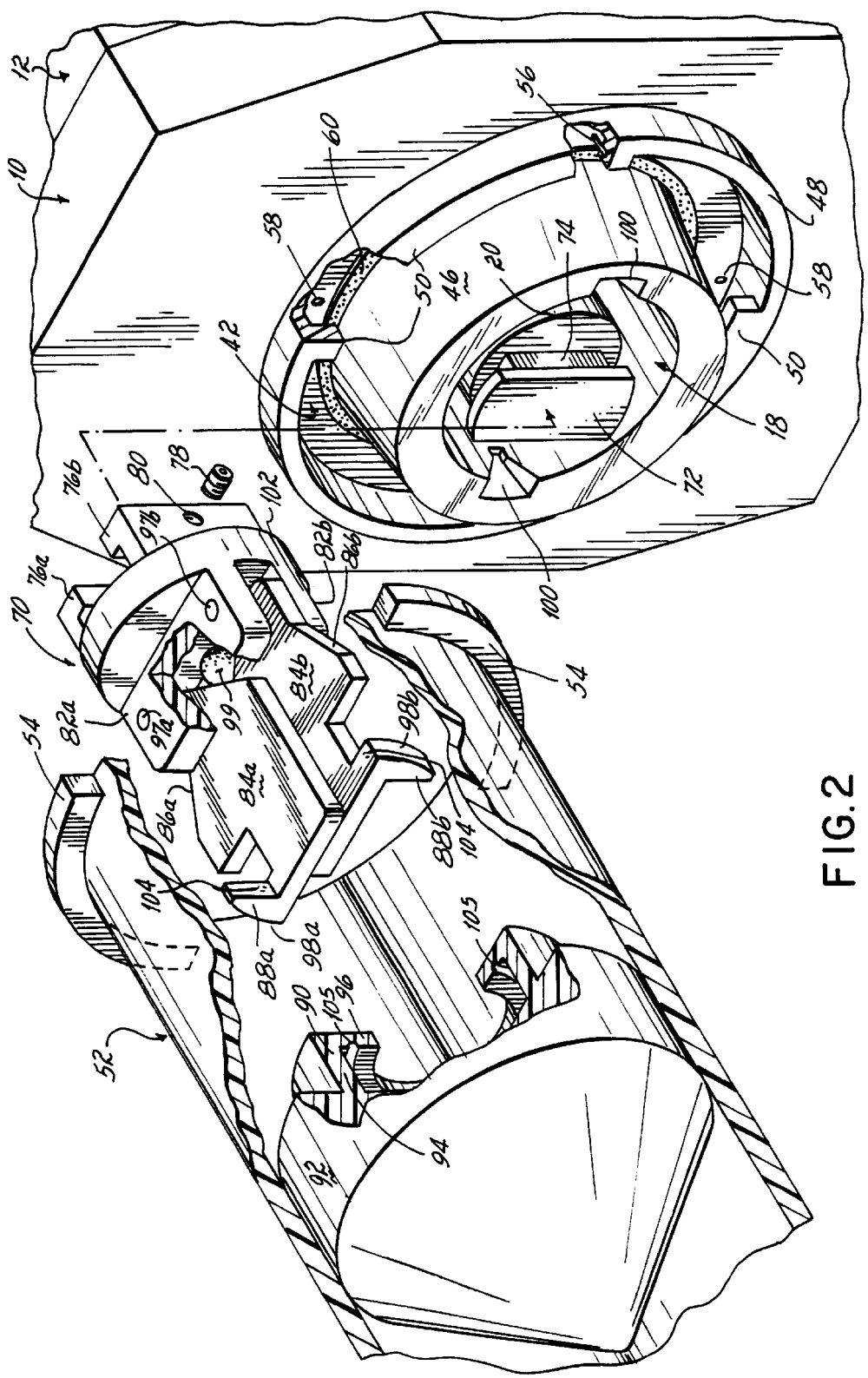
FIG. 2 is a disassembled perspective view of a syringe and ram adapter for use with the face plate illustrated in FIG. 1.

Referring now to FIG. 2, features of a front surface of face plate 10 can be explored. A front surface of face plate 10 includes a channel 42 for receiving a rearward end of a syringe. Channel 42 has a radially inward boundary defined by a cylindrical or slightly conical wall 46, and a radially outward boundary defined by a cylindrical wall 48. To mount a syringe 52 to face plate 10, a rearward edge of a cylindrical wall of syringe 52 is inserted into channel 42 between walls 46 and 48 until this rearward edge of the syringe abuts the floor of channel 42.

Cylindrical wall 48 includes radially inwardly projecting mounting flanges 50 along two alternate sections thereof. Flanges 50 extend approximately ninety degrees angularly about wall 48, and together form a bayonet locking mount for connection to a rearward end of a syringe. Specifically, a syringe such as syringe 52 shown in FIG. 2, includes radially outwardly directed mounting flanges 54. Flanges 54 extend outwardly a distance approximately equal to the radially inward extension of mounting flanges 50 on face plate 10. Further, flanges 54 extend angularly around the circumference of syringe 52 for slightly less than ninety degrees, permitting flanges 54 to be fitted beneath flanges 50.

Syringe 52 as illustrated in FIG. 2, is in position for insertion of flanges 54 on syringe 52 between flanges 50 on face plate 10. After thus inserting the flanges 54 between the flanges 50, syringe 52 is twisted in a clockwise direction through an angle of approximately ninety degrees, to rotate flanges 54 beneath flanges 50. At a clockwise end of flange 50 face plate 10, pins 56 (one of which is shown) extend across channel 52 between flange 50 and the rearward surface of channel 42. When syringe 52 is fully rotated clockwise into position on face plate 10, the clockwise ends of flanges 54 on syringe 52 abut to pins 56. When flanges 54 abut against pins 56, this indicates to the user that syringe 52 is fully rotated into its locked position.

Face plate 10 includes holes 58 in a bottom surface of channel 42 approximately opposite to a counter-clockwise end of each flange 50. Holes 58 are sized to receive locking pins 34 of collar 22 to permit locking pins 34 to extend through holes 58 and across channel 42 to mounting flange 50. When syringe 52 is rotated to its locked position, with flanges 54 positioned fully behind flanges 50 and abutting pins 56, the counter-clockwise end of flanges 54 do not overlap holes 58. Thus, when syringe 52 is in its locked position, pins 34 are permitted to pass through holes 58. The interaction of pins 34 and flanges 54 to perform a locking function will be discussed below with reference to FIGS. 3 and 4.

A region of a bottom surface of channel 42 may include a gasket 60 made of rubber or another resilient sealing material. Gasket 60 seals against a cylindrical rearward surface of syringe 52 to provide a seal between the rearward surface of syringe 52 and face plate 10. As disclosed in further detail in the above referenced U.S. Patent application, inclusion of a gasket 60 in this position obviates the need for sealing flanges or other structures on syringe 52.

FIG. 2 further illustrates a ram tip adapter and extender 70. Adapter 70 is sized to be mounted upon a forward end 72 of the ram of injector 12. As described in U.S. Pat. No. 5,383,858, end 72 of ram 20 has a T-shape coupler including vertically extending sections for engaging a coupling on the rear surface of a plunger of a syringe. In accordance with principles of the present invention, extender/adapter 70 is mounted to end 72 by inserting end 72 into a notch 74 on a rearward surface of extender/adapter 70. Notch 74 is formed by first and second L-shaped retaining members 76a and 76b, which are sized to fit snugly over end 72 of ram 20. A retaining screw 78 fits through a threaded aperture 80 in retaining member 76b to engage a side surface of end 72 of ram 20 to hold extender/adapter 70 in position at an end of ram 20.

Extender/adapter 70 includes, on a forward surface thereof, first and second mounting plates 82a and 82b for retaining therebetween first and second rotating cam/hook members 84a and 84b. Cam/hook members 84a and 84b include cam surfaces 86a and 86b which cam members 84a and 84b into rotation through interaction with face plate 10. Cam/hook members 84a and 84b further include hook members 88a and 88b for connection to a coupler 90 on a rearward surface of a plunger 92 within a syringe 52.

Coupler 90 on syringe 52 comprises a cylindrical and axially extending wall 94 terminating in a planar disk shaped wall 96 which extends radially inwardly therefrom. Hook members 88a and 88b have an arcuate outer surface 98a and 98b which may be inserted into coupler 90 behind disk shaped wall 96 as discussed in further detail below with reference to FIGS. 3 and 4.

Cam/hook members 84a and 84b are coupled to mounting plates 82a and 82b by hinge pins 97a and 97b inserted through plates 82a and 82b, and through a respective one of cam/hook members 84a or 84b. A resilient ball 99 incorporated between plates 82a and 82b (see FIGS. 3 and 4, below) is captured underneath cam/hook members 84a and 84b to create torque tending to cause hook element 88b of cam/hook member 84b to rotate radially outwardly and into engagement with coupler 90 of plunger 92, and cause hook element 88a of cam/hook member 84a to rotate radially outwardly and into engagement with coupler 90.

As seen in FIG. 2, conical wall 46, which extends outwardly around the main aperture 18 of face place 10, includes, on a inner surface thereof, cam surfaces 100 having a generally trapezoidal shape. Cam surfaces 100 interact with cam surfaces 86a and 86b of cam/hook members 84a and 84b when extender/adapter 70 is mounted to the forward end 72 of ram 20.

Figure 4:
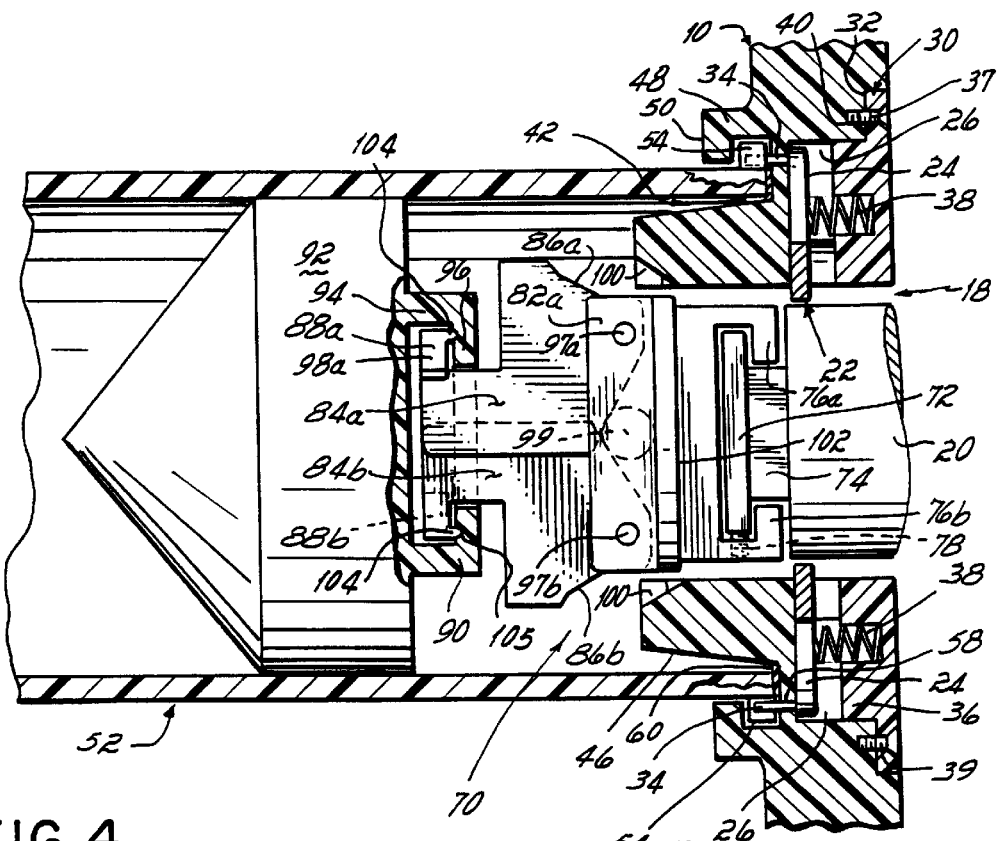
FIGS. 3 and 4 are partial cross-sectional views of the syringe, face plate and ram adapter of FIGS. 1 and 2, showing the interaction of various components thereof when a syringe is mounted to the face plate.
Figure 3:
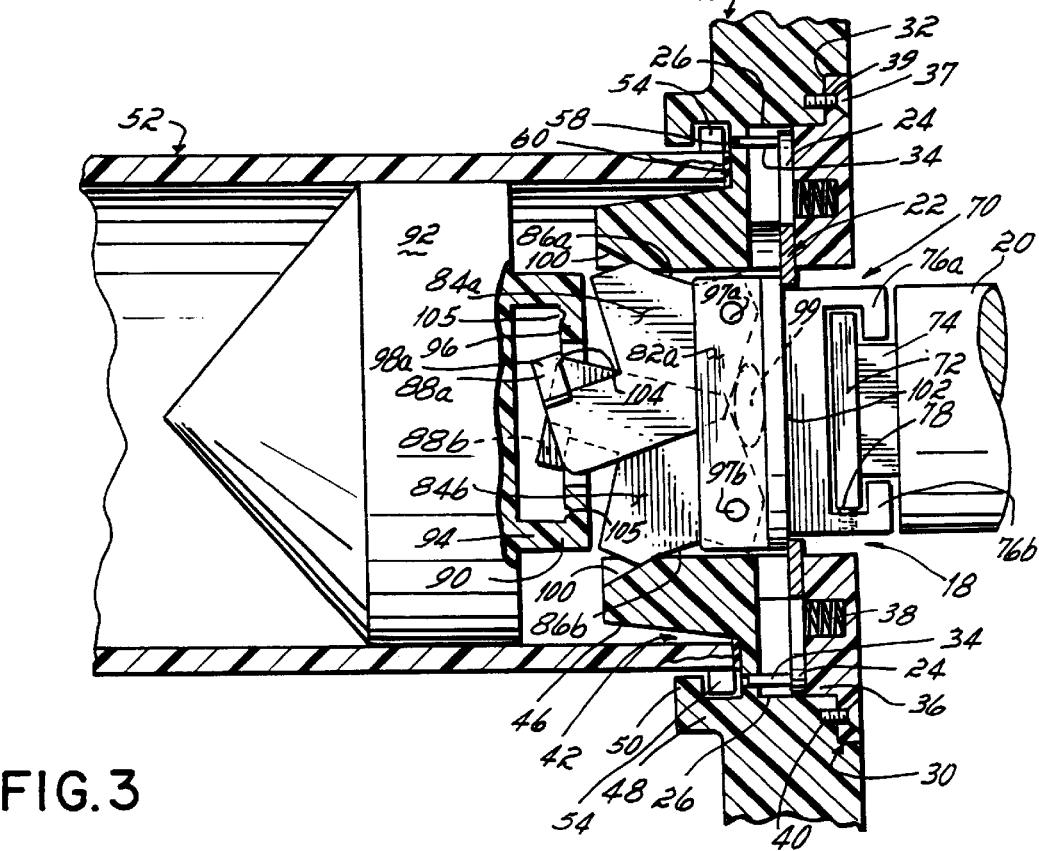

Referring now to FIGS. 3 and 4, specifics of the interaction of extender/adapter 70, face plate 10, ram 20, plunger 92 and connector 90, and cam/hook members 84a and 84b can be more fully described. Specifically, in use, face plate 10 is mounted to injector 12, and then extender/adapter 70 is mounted to end 72 of ram 20 of injector 12, and set screw 78 is threaded through aperture 80 against end 72 to hold extender/adapter 70 in place. To perform this operation, ram 20 is moved forward using manual movement controls of injector 12 (not shown) to a position roughly like that shown in FIG. 2, so that notch 74 of extender/adapter 70 can be fitted over end 70 of ram 20.

Subsequently, when ram 20 moves backward to its rearwardmost position as shown in FIG. 3, extender/adapter 70 interacts with features of face plate 10 to release a syringe locked into face place 10 to permit the removal or replacement of the syringe. Specifically, when ram 20 is at its rearwardmost position such as shown in FIG. 3, cam surfaces 86a and 86b of cam/hook members 84a and 84b contact cam surfaces 100 formed in face plate 10. This contact, combined with rearward motion of ram 20, forces cam/hook member 84a to rotate in a counter-clockwise direction as viewed in FIG. 3, and forces cam/hook member 84b to rotate into a clockwise direction as viewed in FIG. 3, to the positions shown in FIG. 3. In these positions, hook member 88a and hook member 88b are withdrawn to a radially central position shown in FIG. 3, in which these hook members do not engage to a coupler 90 at the rearward face of a plunger 92 and syringe 52 mounted to face plate 10. Accordingly, plunger 92 is disengaged from ram 20 and syringe 52 can be removed from face plate 10 and replaced with a new syringe.

As also can be seen in FIG. 3, when plunger 20 is withdrawn to its rearwardmost position, an outermost surface 102 of extender/adapter 70 interlocks with collar 22 causing collar 22 to be drawn rearwardly into face plate 10 along with extender/adaptor 70 in ram 20. This motion causes locking pins 34 which are integrally formed with collar 22 to withdraw through holes 58 and out of channel 42. (The motion of locking pins 34 along with plate 22 is illustrated in FIG. 3 for illustrative purposes, however it will be appreciated that neither locking pins 34 nor holes 58 would be visible in the cross-sectional view of FIG. 3 because these elements are positioned ninety degrees offset from the cross-sectional plane of FIG. 3.)

Rotation of cam/hook members 84a and 84b to the positions shown in FIG. 3, also compresses ball 99, which generates torque urging cam/hook members 84a and 84b to rotate radially outwardly.

Referring now to FIG. 4, it can be seen that when ram 20 is brought forward for the purpose of initiating an injection with syringe 52, cam surfaces 86a and 86b of cam/hook members 84a and 84b release from engagement with cam services 100 of face plate 10. As a result, due to torque generated by the compression of resilient ball 99, cam/hook member 84a rotates clockwise about hinge pin 97a as viewed in FIG. 4, and cam/hook member 84b rotates counter-clockwise about hinge pin 97b as viewed in FIG. 4, so that hook members 88a and 88b are placed into an engaging position such as shown in FIG. 4. In this position, hook members 88a and 88b of cam/hook members 84a and 84b spread radially outward into engagement with connector 90 of plunger 92. Once in this position, hook members 88a and 88b will engage coupler 90 to permit forward and reverse motion of plunger 92 under drive of ram 20.

Furthermore, as seen in FIG. 4 for illustrative purposes, when ram 20 moves to a forward position, collar 22 is free to move forward in response to resilient force from springs 38, or another resilient element used in place of springs 38. In such a situation, locking pins 34 move forward into channel 42 and adjacent to the ends of flanges 54 of syringe 52. Accordingly, once ram 20 moves to a forward position, locking pins 34 prevent syringe 52 from being rotated to a disengaged orientation.

Thus, once a syringe is mounted onto the injector face plate 10, and the ram 20 is moved forward into the syringe, the operation of collar 22, locking pins 34 and flanges 54 of the syringe will lock the syringe to face plate 10 unless and until ram 20 is moved to its rearwardmost position. This prevents an operator from attempting to remove the syringe from the injector with the ram forward of its rearwardmost position.

Furthermore, plunger 92 of the syringe will be locked to ram 20 unless and until ram 20 returns to its rearward most position. This ensures that plunger 92 cannot be disconnected from ram 20 unless and until ram 20 is at its rearwardmost position.

As seen in FIGS. 3 and 4, hook members 88a and 88b include, on their inner surfaces, dimples 104. When cam/hook members 84a and 84b are in their engaged positions as shown in FIG. 4, dimples 104 engage to a groove 105 in an inner surface of disk-shaped wall 96 of syringe coupler 90. Engagement of dimples 104 to groove 105 reduces the likelihood that cam/hook members 84a and 84b will rotate to a disengaged position when syringe plunger 92 is drawn rearward to fill the syringe. Furthermore, it will be noted that, when cam/hook members 84a and 84b are in their engaged position as shown in FIG. 4, dimples 104 couple to grooves 105 approximately axially opposite to hinge pins 97a and 97b. As a result, substantially little torque on cam/hook members 84a and 84b, about hinge pins 97a and 97b, is generated when the injector is used to draw plunger 92 rearward to fill the syringe; in such a situation, the axially-applied force moving plunger 92 rearward, is roughly parallel to the line between the dimple 104 on a cam/hook member 84a or 84b and the corresponding hinge pin 97a or 97b, reducing the torque on cam/hook members 84a and 84b.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art.

For example, the illustrated structures of face plate 10, including collar 22 and locking pins 34, as well as cam surfaces 100, channel 42 and flanges 50, could be included in an adapter mountable on the existing face plate of the injector shown in U.S. Pat. No. 5,383,858. In such a case, the rear surface of cap 30 could be extended rearwardly to include mounting flanges matable with the face plate illustrated in U.S. Pat. No. 5,383,858 to lock the adapter to the injector's existing face plate. Further, extender/adapter 70 would also be lengthened to compensate for the width of the face plate illustrated in U.S. Pat. No. 5,383,858.

The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A ram tip for a ram of an injector of the type having a housing and a drive ram extendible from said housing for moving a plunger within a syringe, comprising:

a movable member having a connector for engaging a connecting structure on a rearward face of a plunger, and a cam surface for interacting with the injector to move the movable member when the ram tip is in a predetermined position, said connector being movable upon interaction between said cam surface and the injector, between an engaging position in which said connector engages with the connecting structure of the plunger, and a disengaging position in which said connector does not engage the connecting structure of the plunger.

2. The ram tip of claim 1, further comprising a second movable member, said second movable member having a second connector and a second cam surface for interacting with the injector to move the movable member when the ram tip is moved to a predetermined position.

3. The ram tip of claim 2 wherein said second connector is movable upon interaction between said second cam surface and the injector, between an engaging position in which said second connector engages with the connecting structure of the interacting with the injector to move the movable member when the ram tip is in a predetermined position, and a disengaging position in which said second connector does not engage the connecting structure of the plunger.

4. The ram tip of claim 1 configured as a ram, tip adapter, further comprising connecting structure on a surface of said ram tip opposite said movable member, said connecting structure configured for connection to a tip of an original-equipment ram supplied with the injector.

5. The ram tip of claim 1 wherein said movable member is movable by rotating relative to said ram tip between said engaging and disengaging positions.

6. The ram tip of claim 5 wherein said connector is a hook, said hook projecting radially outward when said movable member is rotated into said engaging position, said hook positioned at a radially inward position when said movable member is rotated into said disengaging position.

7. The ram tip of claim 5 wherein said cam surface is a ramp member, configured to contact a mating ramp member on a front surface of the injector, contact between said cam surface and said ramp member causing said movable member to rotate inwardly toward its disengaging position.

8. The ram tip of claim 5 further comprising a resilient element producing a force tending to position said movable member in its engaging position absent a counteracting force applied to said can surface.

* * * * *